United States Patent [19]

Kenet et al.

[11] Patent Number: 5,016,173
[45] Date of Patent: May 14, 1991

[54] APPARATUS AND METHOD FOR MONITORING VISUALLY ACCESSIBLE SURFACES OF THE BODY

[75] Inventors: Robert O. Kenet; Barney J. Kenet, both of Lakeland, Fla.; Guillermo J. Tearney, Cambridge, Mass.

[73] Assignee: Vanguard Imaging Ltd., Cambridge, Mass.

[21] Appl. No.: 337,304

[22] Filed: Apr. 13, 1989

[51] Int. Cl.$^5$ .............................................. G06F 15/92
[52] U.S. Cl. .................................. 364/413.13; 382/6; 382/22
[58] Field of Search ................. 364/413.13; 382/6, 22, 382/25

[56] References Cited

U.S. PATENT DOCUMENTS

| | | | |
|---|---|---|---|
| 4,533,947 | 8/1985 | Smith | 382/6 |
| 4,641,349 | 2/1987 | Flom et al. | 382/6 |
| 4,731,745 | 3/1988 | Katagiri et al. | 382/25 |
| 4,771,469 | 9/1988 | Wittenburg | 382/25 |
| 4,780,907 | 10/1988 | Spieser et al. | 382/6 |
| 4,839,807 | 1/1989 | Doi et al. | 382/6 |
| 4,851,984 | 7/1989 | Doi et al. | 382/413.23 |

Primary Examiner—Michael R. Fleming
Assistant Examiner—Gail O. Hayes
Attorney, Agent, or Firm—Choate, Hall & Stewart

[57] ABSTRACT

This invention relates to an improved apparatus and method for in vivo monitoring of visually accessible surfaces of the body. The invention synthesizes methods of systems identification and computer vision to quantify and/or classify features of surface or subsurface anatomic, physiologic, or pathologic structures or processes. Such is accomplished by the stimulation of anatomic surfaces with light (visible, infrared, and/or ultraviolet, structured or uniform), followed by the quantitative analysis of digital images (multiresolution, multiview, and/or multispectral) of reflected or emitted light from the surface of interest.

15 Claims, 3 Drawing Sheets

APPARATUS AND METHOD FOR MONITORING VISUALLY ACCESSIBLE SURFACES OF THE BODY

BACKGROUND OF THE INVENTION

This invention relates to an improved apparatus and method for in vivo monitoring of visually accessible surfaces of the body. Surfaces, such as the skin are directly accessible, while other surfaces, such as the cervix, the retina, and the vascular endothelium require an optical apparatus to be visibly accessible.

Systems identification is the engineering method whereby parameters of a system, in this case a biological surface, defined by its optical properties, are "identified"—that is quantitatively estimated—using data derived from input and/or output signals of the system. The spatial, temporal, and spectral distributions of light stimulating a biological surface may be considered the input signals to the system, and the spatial, temporal, and spectral distributions of light reflected by or emitted from the system may be considered the output signals of the system.

Computer vision refers to engineering methods whereby images are analyzed, using tools including image processing, quantitative feature extraction, and decision theory, to interpret the contents of the images. Thus, by combining systems identification with computer vision, images of a biological surface, obtained under various lighting and/or viewing conditions, may be used to provide parameters describing features of surface structures or processes.

An example of a surface commonly monitored for abnormalities is the skin. Skin cancer incidence has increased markedly in recent years. Present clinical methods of screening and monitoring cutaneous surfaces for premalignant features include, qualitative assessment, of gross visual features of dysplasia or malignancy (such as asymmetry, border irregularity, color variability, diameter and elevation of skin lesions), and sequential examination, relying on the physician's memory, written descriptions, sketches, and visual inspection of conventional analog photographs, to assist in deciding if a surface lesion is new or has features which have changed. Patients with dysplastic nevi syndrome may have hundreds of pigmented skin lesions which need to be monitored for signs of cancer. A system which systematically (1) monitors the number of lesions and their positions on the body surface, and (2) quantifies morphologic and spectral features of such lesions would provide a useful tool for improving management of this potentially deadly disease.

Another surface routinely monitored for abnormalities is the cervix. Cancer of the cervix is a common cancer in women. Digital colposcopy with simple image enhancement has been shown, anecdotally, to detect premalignant cervical abnormalities in cases where the standard screening test, the Papaniocoloaou smear, was falsely negative.

Another example of a surface where visual examination is essential in order to detect abnormalities or changes is the retina. Retinal imaging is an important method for detecting, monitoring, and guiding therapy for clinical conditions which may lead to blindness. Photogrammetric methods for obtaining three dimensional measurements of retinal structures from analog stereo photographs and simple digital methods for two-dimensional imaging of retinal features are presently in the vanguard of methods used to monitor certain retinal features.

The vascular endothelium, however is the anatomic surface responsible for the majority of deaths in this country (i.e. due to myocardial infarction). The optical apparatus necessary to view it has recently become available in the form of angioscopic catheters, yet no systematic method for analyzing and utilizing images of this surface has been developed.

For each of these visually accessible anatomic surfaces, a coherent synthesis of appropriate digital methods for systems identification and computer vision would improve the detection and monitoring of abnormalities, before, during, and after therapy.

SUMMARY OF THE INVENTION

It is therefore an object of this invention to provide an apparatus and method for (1) the in vivo detection, quantification, and/or classification of features of visually accessible bioloqical surface structures and processes, (2) the monitoring of changes in such features with time or after interventions, (3) the mapping of the surface positions of such features, and/or (4) the reconstruction of 3- and 4-dimensional (3-D as a function of time) surface and subsurface morphology and topology of such visually accessible anatomic surfaces.

These objects of the invention are attained by combining methods derived from systems identification and computer vision with methods of photography that are (1) digital, (2) quantitative, (3) multispectral, (4) multiview, and/or (5) multiresolution. Digital photographic methods provide a computer-based substrate for automatic feature extraction, surface reconstruction, tissue characterization, and feature location mapping. Quantitative digital photography provides the ability to precisely and reproducibly estimate quantitative features of anatomic surface structures or processes. Multispectral digital photography provides the ability to characterize and classify surface structure components and processes, and their temporal-spatial distributions, in particular, the depth of their subsurface extents. Multiview digital photography (or single-view photography with multiple-position or structured-light stimulation) provides the ability to reconstruct three-dimensional surface topology using, for example, stereo, optical flow, photometric stereo, shape-from-shading, moiré, or structured-light methods of three-dimensional surface reconstruction. Multiresolution digital photography provides the ability to map the global surface location of macro- or microscopic surface features.

More specifically, it is an object of this invention to provide an apparatus and method for the aquisition of computer-based digital photographs of skin lesions, permitting, not only efficient storage and recall of visual documentation, but also automatic counting of lesions and mapping of their global body surface locations, and quantitative analysis of visual features thereof, as a means for detecting evidence of dysplasia or malignancy. Further, by means of quantitative comparison with previous images, and the extracted features thereof, the detection of new skin lesions and changes in morphologic and colorimetric spectral features of existing lesions may be achieved.

Moreover, it is yet another object of this invention to provide an apparatus and method for the simultaneous digital acquisition of color and infrared photographs of skin, permitting the implementation of a novel quantitative algorithm for estimating the depth and volume of certain cutaneous structures or processes. Such estimates are virtually impossible with routine analog photography. Since depth of invasion is one of the most important prognostic features of melanoma, such a method for imaging below the surface of the skin would provide important clinical information that cannot be obtained with present methods of noninvasive clinical examination. In addition, other types of spectral algorithms may be applied to such multispectral images to characterize the spatial distribution of the various light absorbing components of skin, including pigments, hemaglobin, and bilirubin.

Similarly, it is an object of this invention to provide an apparatus and method which, when combined with appropriate clinical examination equipment, may provide the ability to quantify features of multispectral digital photographs of the cervix in an effort to enhance the diagnostic accuracy of colposcopic examination. In addition, it is yet another object of this invention to provide an apparatus and method which may be applied to quantitative, automatic, three-dimensional retinal imaging, with quantification and classification of anatomic and physiologic features thereof, thus providing improved methods to detect and monitor retinal pathology. By quantifying 3-dimensional features of the topology of retinal surfaces and the retinal vasculature, such methods may provide the means for improved management of retinal detachment, glaucoma, and diabetic retinopathy.

Moreover, it is yet a further object of the invention to provide an apparatus and method, which when combined with an apparatus that provides visual accessiblity, would permit in vivo multispectral inspection and tissue characterization of the coronary artery endothelium in the region of atheromatous plaque. Such may be accomplished by imaging reflected light of one or more wavelengths passed through an angioscopic catheter, followed by multispectral image analysis and tissue parameter identification. Such a technique could provide a novel method for precisely controlling laser angioplasty of coronary artery lesions or of other lesions in other vascular structures.

Thus quantitative, digital, multispectral, multiview, and/or multiresolution photography of visually accessible anatomic surfaces, in vivo, with quantitative feature estimation and/or tissue characterization may provide important advances in clinical management of a variety of diseases. The technology, in addition, has commercial applications in nonmedical areas such as for the quantitative estimation of skin, hair, and eye color, or skin texture and dryness, for use in the choice of cosmetics.

BRIEF DESCRIPTION OF THE DRAWINGS

The drawing is briefly described as follows.

DESCRIPTION OF THE PREFERRED EMBODIMENTS

A system for monitoring visually accessible surfaces of the body is divided naturally into two parts. The first part consists of the hardware of the system and the second consists of the software or programs which cause the hardware to function as desired. This software however may be implemented directly in hardware.

Hardware

Figure 1:
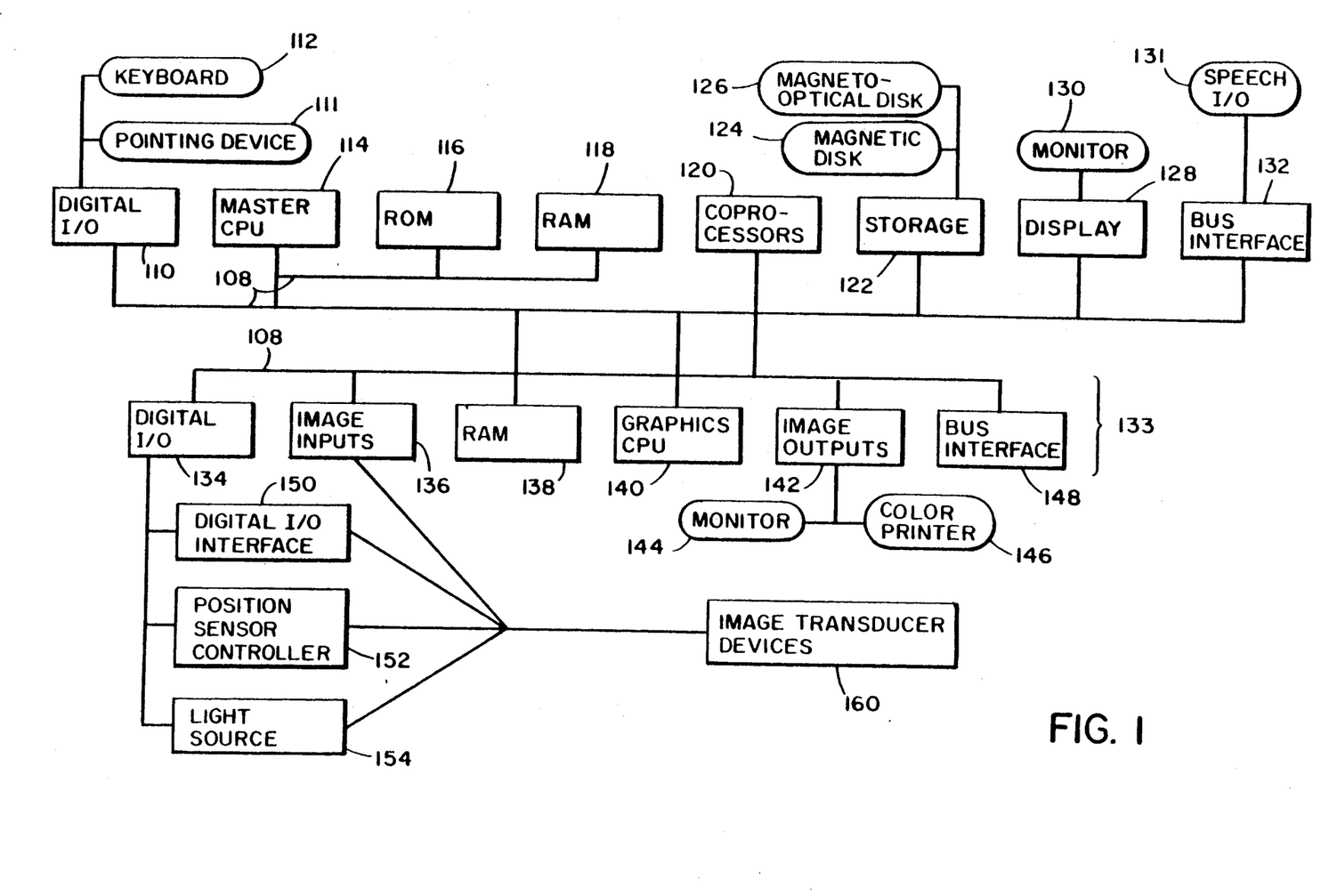
FIG. 1 is a block diagram of an embodiment of the hardware of the invention.

The hardware for a system for monitoring visually accessible surfaces in vivo is shown in FIG. 1. A master central processing unit (CPU) 114 is connected by one or more buses 108 to the following apparatus: a read only memory (ROM) 116, a random access memory (RAM) 118, one or more digital input/output ports 110 to which are attached one or more input devices such as a keyboard 112 and a pointing device 111, a display controller 128 to which is attached a display monitor 130, one or more storage device controllers 122 to which are attached one or more magnetic, optical, magneto-optical, or digital paper disk or tape drives or other storage device 124 and 126, a bus interface for interfacing additional hardware 132, a frame store or imaging subsystem 133 capable of at least 24 or 32 bit color image acquisition, processing, and display, and one or more optional coprocessors 120 to increse computation speed.

The frame store or imaging subsystem 133 includes one or more image input ports 136, random access memory (RAM) 138 for storing images, data, and/or microcode, a graphics CPU or coprocessor 140, one or more digital input/output ports 134, one or more image output ports 142, and an optional bus expansion interface 148. The coprocessor 120 may be configured to communicate directly with the graphics CPU 140 and the frame store RAM 138.

The image input port 136 is connected to one or more image transducer devices 160 described below. The digital input/output port(s) 134 are connected to one or more digital input and/or output devices. For example, it may be connected to a digital input/output interface 150 for reading the status of one or more buttons or switches (222 FIG. 2(a)) contained in the image transducer device 160, and it may be connected to an optional position sensor controller unit 152 which converts information from a position sensing element (224 FIG. 2(a)) contained in the image transducer device 160.

The digital input/output ports 110 and 134 and the bus interfaces 132 and 148 provide the flexibility to add additional devices such as a speech input/output device 131 for the convenience of the operator or to provide verbal instructions to the operator and/or patient.

The image input port 136 contains a set of analog-to-digital converters (A/D), for example four parallel A/D's, for use with an analog image transducer device 160. Alternatively it may also include appropriate digital input hardware for use with a digital image transducer device 160. Each A/D in the image input port 136 converts an analog signal from an image sensor contained within the image transducer device 160 to digital values for storage in the RAM memory 138 of the frame store or imaging subsystem 133. The memory 138 stores one or more digital images of programmable size (up to at least 1024×1024) and pixel depth (up to at least 32 bits). The data may be rapidly converted to other digital values before storage in memory 138 by means of a set of input look-up-tables (also contained in the image input port 136). After storage it may be mathematically manipulated by the graphics CPU 140, master CPU 114, and/or additional coprocessors 120. The data is then read (via output look-up-tables) by a set of digital-to-analog converters (D/A's) contained in the image output port 142 and displayed on a 2-dimensional, or 3-dimensional stereo, video display monitor 144. The output port 142 may contain additional hardware for driving other types of displays, for example a 3-dimensional holographic display. The image output port 142 is also connected to a color hardcopy printer 146.

Image transducer device

Figure 2A:
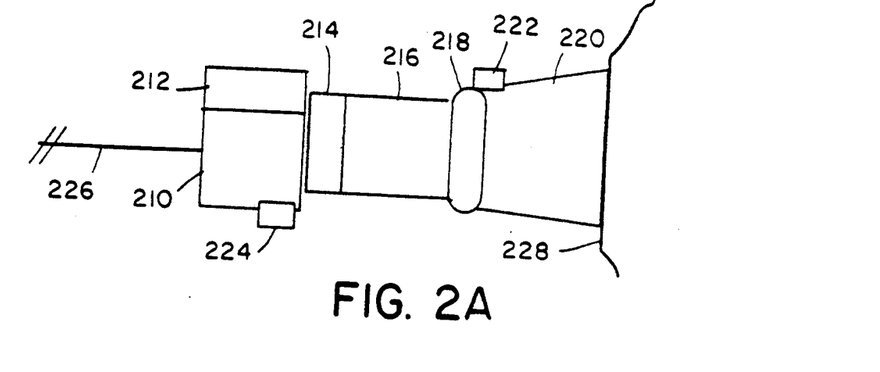
FIGS. 2a–2c are a block diagram of sample embodiments of the image transducer apparatus components of the hardware of the invention.
Figure 2B:
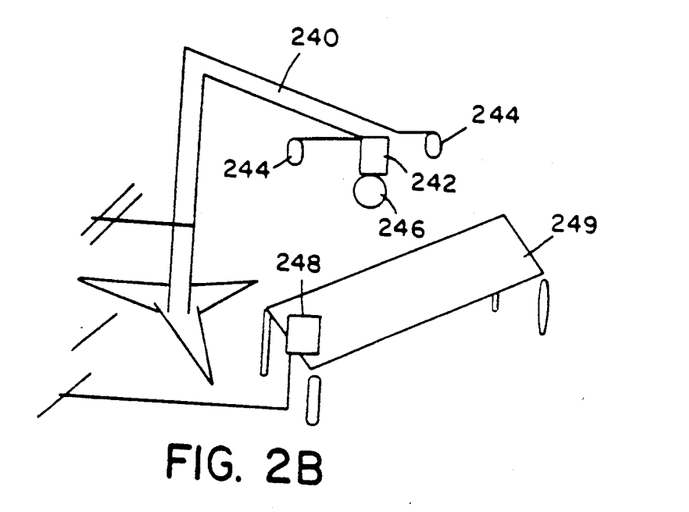
Figure 2C:
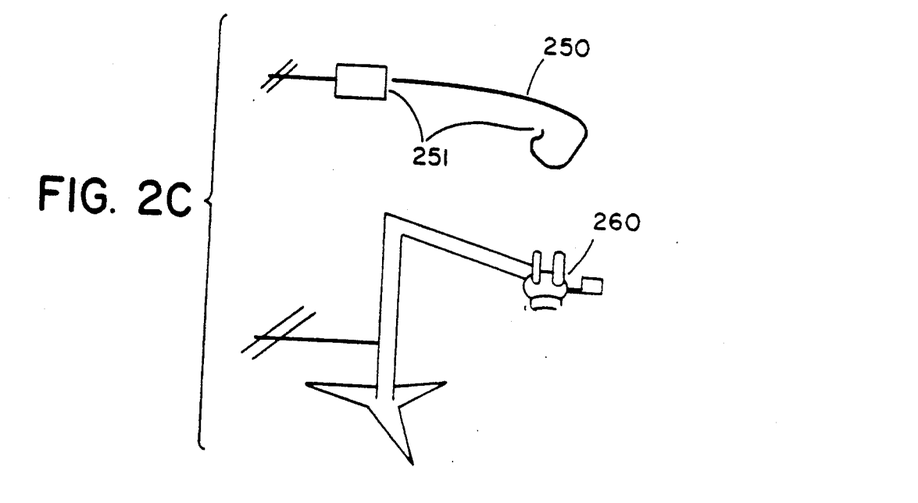

The image transducer device 160 may contain one or more cameras or other imaging devices which may be directed to view a visibly accessible anatomic surface of a patient or subject, either through one or more lenses with appropriate beam splitters, filters, filter wheels, or shutters, if necessary, or through an examination microscope, colposcope, or ophthalmoscope 260 (FIG. 2(c)) or angioscope 250 (FIG. 2(c)) with appropriate image sensors 251, or by means of other optical or electro-optical apparatus. The image sensors contained in the image transducer device may be monochromatic, color, and/or infrared, and may consist of one or more charge-coupled devices (CCD), vidicon tubes, confocal laser scanners, or other type of image sensor with appropriate filters where necessary. An R-G-B color camera ideally should have precise registration between the red, green, and blue imaging sensors.

A preferred embodiment of the image transducer device 160 is illustrated in FIG. 2(a) and FIG. 2(b). In this embodiment the device is divided into a global surface image transducer device (FIG. 2(b)) and a local surface image transducer device (FIG. 2(a)). The global surface image transducer device (FIG. 2(b)) is designed for the purpose of obtaining images with a field of view encompassing a relatively large, i.e. global, portion of the visible anatomic surface under examination. Global images may be used as maps onto which the location of higher magnification images, obtained with the local surface image transducer, may be recorded, either manually by the operator, or by use of an input device (e.g. a pointing device 111), or automatically by means of an automatic position sensor 224, 248, and 152. The image input ports 136 may be configured to switch, under software or operator control, between the global and local surface image transducer devices; or if necessary, a video switching device, controlled via the digital input/output port 134, may be interposed between the image transducer devices 160 and the input ports 136.

Global image transducer

The global image transducer device (FIG. 2(b)) consists of one or more video or digital cameras or other image sensing devices 242 with appropriate lenses such as wide angle or remote controlled zoom lenses 246 and illumination sources 244 which illuminate a large or "global" region of the anatomic surface with uniform and/or structured light. The apparatus may be mounted on a stand 240 over a patient examination table 249 or alternatively on a computer controlled robot positioning arm 240. The stand or robot arm 240 may also be configured to direct the camera(s) (or other image sensor(s)) 242 to view a standing or sitting, rather than a supine, patient or subject. The source element for an automatic position sensing device 248 may be mounted on or near the examination table 249 or, for a standing patient, anywhere near the location where the patient or subject stands during global surface examination.

Local image tranducer

The local surface image transducer device (FIG. 2(a)) is designed to obtain a magnified view of a relatively smaller, i.e. local, field of view of the anatomic surface 228 under examination. The local surface image transducer is designed to simultaneously transduce true color and infrared (or other multispectral set of) images of reflected and/or emitted light from the anatomic surface under examination. An R-G-B video or digital camera 210 (e.g. with three CCD sensors) and an infrared video or digital camera 212 (e.g. with the same type of CCD chip as the R-G-B camera) are both attached via a beamsplitter 214, with appropriate optics for matching the optical distance between the lens and the imaging plane of each device, to a macrolens 216, which is supported by a positioning cone 220 made of non-metallic or metallic material. The positioning cone 220, which may rest directly on an accessible anatomic surface 228, acts to simplify and speed image acquisition by providing a fixed working distance between the imaging device and the anatomic surface.

Illumination may be provided by an annular fiberoptic light guide 218, mounted between the macrolens 216 and the positioning cone 220, such that white, colored, monochromatic, coherent, or structured light is directed uniformly within the positioning cone. The type of light transmitted through the fiberoptic light guide is controlled by the light source 154 (FIG. 1) which may contain multiple light sources and filters under electronic control by the digital input/output interface 150 or port 134. However, a single white light source may be used to obtain four simultaneous images—red, green, blue, and infrared— in this embodiment, when four parallel analog-to-digital converters are contained in the image input controller 136 of FIG. 1. If an ultraviolet source is included in the light source module 154, or directly inside the local surface image transducer, then a sequential image of ultraviolet-stimulated fluorescence of the anatomic surface may be obtained. The illumination may be polarized by including a polarization device anywhere between the light source 154 and the positioning cone 220, for example, as a flat, round polarization filter between the annular fiberoptic light guide and the positioning cone 220.

The local surface image transducer FIG. 2(a) is designed to be hand held and contains one or more tactile-feel pushbuttons (or other type of switch) 222 which are used by the operator to control the hardware and software, for example to signal the apparatus of the exact instant to acquire one or more images from the image transducer apparatus, to switch between the local and global transducers, or to calibrate the position sensor device 152.

The sensing element 224 of the position sensor device 152 is mounted at a fixed location on the local surface image transducer device, whereas the source element 248 is mounted at some reference position, for example on or near the examination table 249. Thus the location of a high magnification image obtained by the local transducer may be mapped onto a low magnification image obtained by the global transducer.

A small, removable calibration structure or chart, of known shape, size, and or color(s), may be placed at the distal opening of the positioning cone 220 during the acquisition of an image for the purpose of calibrating for spatial, intensity, and spectral measures.

Note that there are a number of alternative configurations for these image transducing devices. For example, the positioning cone 220 and annular fiberoptic light guide may be replaced by an integrating sphere and a set of fiberoptic bundles respectively. The macrolens 216 may be replaced by a zoom lens or by a stereo macrolens pair, and the infrared camera 212 may be replaced by another R-G-B camera to obtain stereo color images for image surface reconstruction. Alternatively, two R-G-B cameras 210 and two infrared cameras 211 may be connected via an additional beamsplitter 214 to a stereo macrolens system 216 for use in both stereo surface and stereo subsurface reconstruction. Moreover, multispectral images may alternatively be obtained by substituting a single camera with a filter wheel (under digital control via the digital input/output port 134) for the camera pair 210 and 211 and the beamsplitter 214, repsectively.

Lighting hardware

Lighting conditions may be uniform or structured with respect to space and/or the electromagnetic spectrum. For example, spatially uniform white light may be provided by a white light source connected to an annular fiberoptic ringlight or integrating sphere. Spatially structured light, such as the stripes, random dot patterns, or moiré patterns used with certain three-dimensional surface reconstruction algorithms, may be provided by a white light source with an appropriate set of filters and/or slides or by a laser with appropriate electro-optical apparatus. Spectrally structured light may be provided by an appropriate set of filters with a white light source, or by one or more lasers (e.g. a laser that emits ultraviolet light, which may be used to stimulate melanin fluorescence). Lighting conditions may be standardized to a set of spectral and spatial distributions (e.g. spatially uniform white light of a known color temperature and intensity which contains a known distribution in the near infrared region). Polarization devices may be used, in addition, to minimize specular reflections.

Electro-optical image guides, filters, switchers

Images are obtained from one or more imaging devices and from one or more spatial positions, simultaneously, or sequentially, to permit, for example, multispectral acquisition (e.g. R-G-B color, infrared, and ultraviolet stimulated fluorescense) or photogrammetric or photometric stereo, or optical flow three dimensional image reconstruction. An optical device may be used to permit the acquisition of multipsectral or multiple view images. For multispectral imaging from one view, one or more beam splitters with appropriate spectral properties or other optical device may be used to direct the image from one view to two or more image sensors, or alternatively one or more filters may be automatically switched in and out of the image path, either mechanically or electro optically, to permit the sequential acquisition of images with different spectral characteristics. If images from more than one view are required, for example for stereo imaging, then images from two or more lenses may be directed sequentially to a single set of image sensors by means of an electro-optical or mechano-optical switch. Alternatively, an electronic switch may be used to rapidly switch between image sensors which view the same object from a different spatial position or with a different spectral sensitivity. A calibration ruler, grid, chart or other structure may be imaged and used for automatic calibration for spatial measures, gamma correction, and color.

Position sensor

The three dimensional coordinates of the field of view of the image transducer with respect to the patient are sensed by a three dimensional position sensor which is mounted on or near the image transducer. The output of the position sensor is input to the computer via an input output port 134, or 110 or bus interface 148 or 132.

Software

Figure 3:
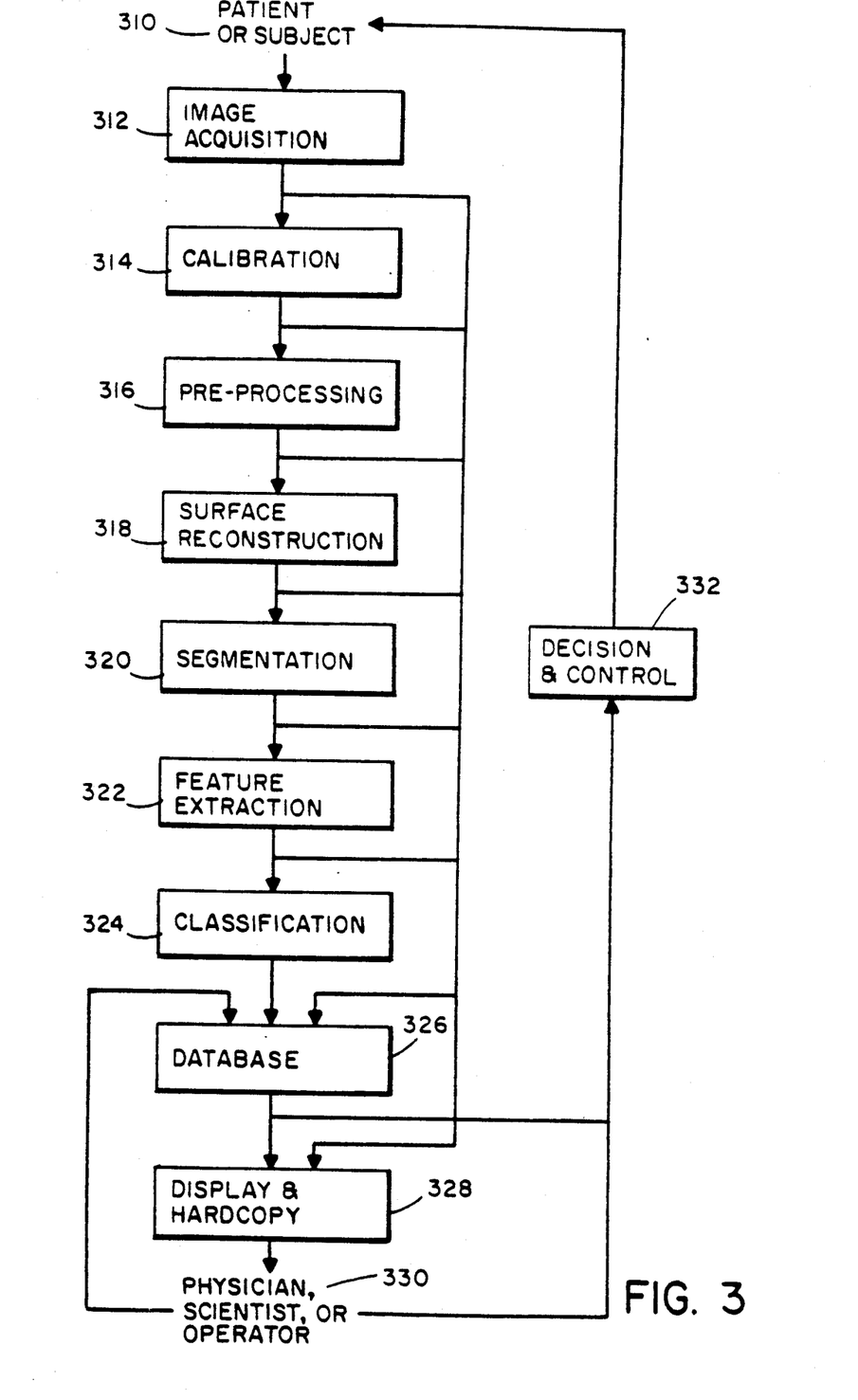
FIG. 3 is a block diagram of system functions for an embodiment of the invention.

FIG. 3 is a block diagram of the system functions and information flow in the system described below. These functions may be implemented in software, firmware, or hardware. The discussion below is for an embodiment of these functions in software.

Initialization

Upon system boot the master CPU 114 (FIG. 1) executes the system programs stored in the system ROM 116 and initializes the system. The programs for monitoring anatomic surfaces are read from magnetic disk 124 into RAM memory 118 and 138 and are executed by the master CPU 114, graphics CPU 140, and additional coprocessors 120 if installed. These programs specify a set of default routines, protocols, algorithms, parameters, and hardware devices which are to be employed during image acquisition 312 (FIG. 3) analysis 314,316,318,328,322,324, storage 326, display 328, and, if appropriate, computer-aided decision, management, or control 332.

Setup

Upon execution of the surface monitoring programs, a control display screen may be displayed on a video monitor 144 and/or 116. Using one of the several input devices 111,112,222, or 131, the operator 330 may execute a setup routine which allows one to change the default routines, protocols, algorithms, and parameters which were set during initialization above and which are described below. The opeartor 330 may choose, for example, a multiresolution, multiview, multispectral, and/or multi-illumination acquisition protocol. These and other choices will determine the specific hardware (FIGS. 1, 2), system functions (FIG. 3), and algorithms that will be employed during image analysis 314,316,318,328,322,324, storage 326, display 328. The operator 330 may choose to turn on or off the following optional system functions—surface reconstruction 318, classification 324, and decision and control 332. The operator 330 may also choose whether the system functions will proceed automatically, with only minimal operator input, or manually with additional opportunity for the operator to change or choose the specific routines and parameters employed by the functions as they proceed.

Image Acquisition (312)

acquisition protocol

Referring to FIGS. 1 and 3, upon the command of the operator 330 one or more images (as determined by the initialization and setup routines) of a region of interest on the anatomic surface (e.q. 228) is acquired. The command may be entered through a pushbutton switch located on or near the image transducer device 222, the keyboard 112 or pointing device 111, or for added convenience may be issued verbally and interpreted by the speech processing unit 131.

The command to capture an image results in the storage of one or more frames of data (as determined by the initialization defaults and the setup choices) in the frame store RAM memory 138. Coincident with the acquisition of an image, the 3-dimensional spatial coordinates of the imaging transducer 160 may be sent via the position sensor controller 152 to one or more of the CPU's 140, 114, or 120 for further processing and subsequent position mapping on a global reference image or synthesized surface map. This acquisition sequence may be repeated to acquire an arbitrary number of images from different locations on the surface. Numerous variations of this acquisition protocol may be chosen by the operator 330 during the setup routine described above.

automatic aspect ratio correction

As determined by the choice of acquisition hardware and software in the initialization and setup routines above, software commands which control the A/D converters in the image input port 136 and the graphics CPU 140 are used to control the input aspect ratio of the captured video image. For example, even though the aspect ratio of a standard NTSC video signal is 4:3, it may be captured with a 1:1 aspect ratio by adjusting horizontal and vertical zoom commands which control the factor by which a pixel clock signal is divided before it is used to drive the A/D converters. The ability to convert to a 1:1 aspect ratio during the analog to-digital conversion process simplifies the computations involved in subsequent quantitative feature extraction and permits the use of a high resolution display screen with a 1:1 aspect ratio where multiple images and graphics materials may be simultaneously displayed. This variable input zoom may also be used to rapidly switch between cameras with different types of video signals as specified by the acquisition protocol chosen in the setup routine above.

multiresolution acquisition

If so determined during the initialization and setup routines, under the control of one or more input control devices 222,111,112,131, images are acquired at two or more resolutions or magnifications. This may be accomplished by using two different image transducers or a single image transducer with changes in the optical or electro-optical device which focuses the image onto the image transducer. For example, the first set of images may be acquired from an image transducer device which has a field of view encompassing a large portion of the visibly accessible surface (i.e. low magnification), for example by a camera mounted above a supine patient, or at a fixed distance from a standing patient (FIG. 2(b)). This first set of images should encompass most of surface at low magnification in a small number of views. They are thus "low resolution" images and will serve to provide a map of the global positions of subsequent "high resolution" or high magnification images which have smaller fields of view, with respect to the overall anatomic surface, or region thereof. The position of the high-magnification images are manually (e.g. via an input device 222,111,112, or 131) or automatically (e.g. using the position sensor 152,224, and 248), recorded on the large field of view images.

In addition, multiresolution images, each with the same field of view, may be acquired in rapid sequence, using a single image transducer with a single setting of the optical apparatus, simply by changing the horizontal and vertical pixel clock divide or zoom, factors of the analog to digital converters in the image input module 136. For example a small size image, for use as an image icon on the display screen 144, may be acquired immediately after a full size image, by increasing the horizontal and vertical pixel clock divide (zoom) factors, or multiresolution pairs of stereo images may be acquired for use with multiresolution hierarchical, stereo matching algorithms.

multispectral acquisition

If so determined during initialization and setup, multispectral images are acquired simultaneously from image transducing devices, and accompanying optical apparatus, with different spectral sensitivities, by using more than one analog to digital converter (in 136) simultaneously. Alternatively they may be acquired in rapid succession by using only one image transducer device 160 and either a set of different lighting conditions or a set of filters in the image transducing device 160.

multiview acquisition

Images obtained from a set of different viewing positions may be acquired simultaneously or in rapid sequence under software control of one or more parallel A/D converters and/or control of an electro optical light guide switch or electronic switch that controls a choice of inputs to the A/D converters. Multiview acquisition is necessary for stereo imaging or for obtaining a time sequence of images from a set of viewing positions in order to use optical flow methods to study spatial geometry of an anatomic surface.

multi-illumination

If so determined during initialization and setup, images of reflected or emitted light, are obtained under a set of different lighting conditions (e.g. structured light for 3-D surface reconstruction or ultraviolet stimulation to study tissue fluorescence), in rapid sequence under software control of the lighting apparatus 154 and the image input module 136.

Calibration (314)

Once an image has been captured, calibration 314 of the image is performed to calibrate for absolute distances and to correct for spatial, color, or intensity distortions due to the acqution equipment and circumstances.

spatial calibration

An image of an object of known size may be used to calibrate for absolute distance in an image obtained at a fixed or known working distance and magnification. For example, an image of a ruler or grid may be obtained during a calibration session, or simultaneously with the image of the surface structure of interest. This ruler or object of known structure and size may be automatically detected using this a priori knowledge with computer vision methods or manually indicated by the operator 330 using a pointing device 111. Once detected, distances between, or sizes of features of, this object, or ruler may be computed by counting pixels. Then, given the known actual distances between, or sizes or intensities of, these features, the absolute size of a pixel at this magnification may be computed and stored for subsequent use as a scale factor, which, when multiplied by the number of pixels of an image feature, results in an absolute distance or size measure of the feature. A similar method to calibrate for image grey levels and nonlinearities thereof may be employed.

color calibration

For color calibration, a color chart, or set of light emitting diodes, of standard known colors, may be imaged, either during a calibration session or during the acquisition of images of the surface feature under examination. If the color chart has a known structure such as vertical stipes, then its features may be detected automatically, using computer vision methods, or semi-automatically with operator input (for example through a mouse or other pointing device 111). Regions of the image containing known colors may be used to identify the set of pixel values representing that color. This set of pixel values (e.g. red, green, and blue pixel values) for an individual known color may then be used to determine input look-up table values, or pixel scaling factors to apply to all pixels of an image that will result in standardization of color between images obtained under similar lighting conditions. This procedure may also be used to calibrate color measurements to absolute wavelength if the wavelengths emitted or reflected by the calibration objects are known a priori. Numerous variations on this method of calibration may be employed by the invention.

fixed background noise subtraction

Fixed background noise of an image sensor (for example due to inoperative pixels in a charge coupled device array) may be obtained under appropriate stimulus conditions and digitally subtracted from each image.

distortion correction

Geometric distortions due to the image transducer device, including its associated optical apparatus, may be corrected using, for example, spatial warping algorithms.

aspect ratio correction (computational)

Under circumstances where the aspect ratio has not already been adjusted to the ratio appropriate for a particular application (such as for an additional display device), it may be adjusted using software subsampling or interpolation algorithms.

Pre-Processing (316)

Pre-processing 316 of an image may be performed, if so determined by the initialization defaults and setup choices, to transform the images to different color space representations (e.g. red-green-blue to hue saturation-intensity or luminance chrominances).

color space transformations

Color video images are usually acquired as three separate red (R), green (G), and blue (B) images. R-G-B images may be transformed to one of several alternative color space representations including, for example, a Hue-Saturation-Intensity (HSI) perceptual color model or a luminance-chrominance model such as the Y-I-Q model used for broadcast television.

hue-saturation-intensity transformation

In one version of the HSI model the hue (H), saturation (S), and intensity (I) values for each pixel may be obtained from the red, green, and blue values as follows:
(1) define
  $R' = R - \min(R,G,B)$
  $G' = G - \min(R,G,B)$
  $B' = B - \min(R,G,B)$
(2) if $B'=0$, then $H=(120*G')/(R'+G'+B')$,
 if $R'=0$, then $H=[120*(B'+1)]/(R'+G'+B')$,
 if $G'=0$, then $H=8\ 120*(R'+2)]/(R'+G'+B')$,
(3) $S=(R'+G'+B')/(R+G+B)$,
(4) $I=(R+G+B)$.

Numerous variations on these models exist and any may be employed by the invention. Thus a single R-G-B image, with a 3-component vector value for each pixel, may be transformed into a number of scalar images, each with a single scalar numerical value for each pixel—i.e. individual images displaying the hue, saturation, or intensity of the image in addition to the obvious scalar images displaying the red, green, or blue components of the original image.

multispectral generalization of HSI transformation

The invention extends this model to higher dimensional multispectral images. For example, given a multispectral image with 4 components—R, G, B, and infrared (IR)—a "4-dimensional" generalized HSI model may be derived as follows:
(1) define
  $R' = R - \min(R,G,B,IR)$
  $G' = G - \min(R,G,B,IR)$
  $B' = B - \min(R,G,B,IR)$
  $IR' = IR - \min(R,G,B,IR)$, then
(2) if $B'=0$, then $H=A/(R'+G'+B'+IR')$,
 if $IR'=0$, then $H=B/(R'+G'+B'+IR')$,
 if $R'=0$, then $H=C/(R'+G'+B'+IR')$,
 if $G'=0$, then $H=D/(R'+G'+B'+IR')$,
 Where
 $A = (90*G')$
 $B = [90*(B'+1)]$
 $C = [90*(IR'+2)]$
 $D = [90*(R'+3)]$
 A, B, C, and D may also take on other values in alternative embodiments of the invention.
(3) $S=(R'+G'+B'+IR')/(R+G+B+IR)$,
(4) $I=(R+G+B+IR)$.

spectral projection

The invention presents a novel method of obtaining a scalar image from an R-G-B (or other multispectral)image that estimates (subject to the spectral limitations of the apparatus that acquired the original image) the scalar image that would have been obtained had the image been acquired through a narrow bandpass filter with a particular hue. This is performed by mathematically projecting the R-G-B color vector for each pixel of an image onto the R-G-B color vector of the given hue. Since the R-G-B color space may be modeled as a Euclidian space, projection of one vector onto another may be performed by obtaining the dot product of one vector on the other. Thus, given the R-G-B color vector of the filter with the desired hue C(c1,c2,c3) (for example yellow (R=1,G=1,B=0), cyan (R=0,G=1,B=1), or magenta (R=1,G=0,B=1), the vector to scalar transformation may be performed as follows:

$F_{i,j} = (R,G,B)_{i,j} \cdot (c1,c2,c3)$ $= (R_{i,j}*c1)+(G_{i,j}*c2)+(R_{i,j}*c3)$ for each pixel position i,j, where $F_{i,j}$ is the resulting transformed image, and where $R_{i,j}$, $G_{i,j}$, and $B_{i,j}$ are the red, green, and blue components of the i,j$^{th}$ pixel of the original image. Note that * indicates multiplication.

This method permits the simultaneous acquisition of an arbitrary number of multispectral images simply by acquiring a single R-G-B image. These multispectral images must, however, have hues (or wavelengths) contained within the R-G-B space.

Surface and Subsurface Reconstruction (318)

The image, after calibration 314 and pre-processing 316, may be stored in the database 326 for later retrieval and/or may undergo immediate analysis 318, 320, 322, and/or 324. If an appropriate multiview or multiple illumination acquisition protocol was specified by the initialization and setup routines above, then these images may be used to reconstruct a 3-dimensional surface map of the anatomic surface in step 318 using one of several reconstruction methods. If, in addition, a temporal sequence of such images has been acquired, then a 4-dimensional (3-D space plus time) reconsturction of the surface as it varies in time may be obtained, by sequentially reconstructing a 3-dimensional surface for each point in the temporal acquisition sequence. A 4-dimensional reconstruction of the surface may be used to estimate mechanical or motion-related properties of the surface.

3-D surface reconstruction

A variety of 3-D surface reconstruction algorithms may be implemented by the invention if the appropriate images were acquired during the acquisition sequence. For example, if stereo pairs of images were acquired, a variety of stereo matching and triangulation algorithms may be employed to obtain the elevation of the surface. Alternatively, other methods such as photometric stereo, structured light, moiré, or optical flow may be employed if the appropriate lighting conditions and/or motion sequences were employed during image acquisition.

One embodiment of this system function 318 for a pair of binocular stereo color images consists of the following steps:

(1) Obtain color space transformation (R-G-B to H-S-I and Y-I-Q) of the original left and right images as described in the pre processing step 316. The following steps may be applied to one or more of the nine resulting scalar images, i.e. R,G,B,H,S,I (intensity), Y,I (chrominance), and Q.

(2) Operate on left and right image pairs with one or more directional Sobel edge operators.

(3) For each of the resulting gradient images eliminate all pixels except those which are local maxima. Then threshold the resulting images using a predetermined or computed pixel value, for example the midpoint of all possible pixel values—i.e. 128 for an 8-bit pixel. The resulting thresholded gradient images may be used as feature points for a stereo matching algorithm, such as the one described in the following steps:

(4) For each stereo pair of thresholded gradient images determine the location of corresponding epipolar lines in the left and right images. Place a window of predetermined size on the first feature point of the first epipolar line in the left image of a stereo image pair.

(5) Then search along the corresponding epipolar line in the right image using a sequential similarity different algorithm (SSDA) to minimize a distance measure, $D_w$, between one or more stereo pairs of left and right thresholded gradient images, within a window, w, of size, n by m pixels, as follows:

$$D_w = \sum_{j=1}^{m} \sum_{i=1}^{n} (F_L(i,j) - F_R(i,j))^2 / V_w$$

where $F_L$ is the left image, $F_R$ is the right image, $V_w$ is the variance within the window w, and i and j are the horizontal and vertical pixel position indices within the window.

(6) Determine the window location along the right epipolar line where $D_w$ is minimum.

(7) If the minimum $D_w$ is below a predetermined matching threshold, then consider the pixels in the center of the window in the left and right images as a pair of matched points. If the minimum $D_w$ is above the predetermined matching theshold but below a predetermined ambiguous match threshold, then increase the size of the window and repeat steps 5 to 7 until either a match occurs or until the minimum $D_w$ is above the ambiguous match threshold.

(8) Shift the left window to the next feature point along the left epipolar line and increment to the next epipolar line pair, if necessary, and repeat steps 5 to 7 until the SSD algorithm has been applied to all feature points in the left and right images.

(9) Triangulate to obtain the 3-D surface elevation for each pair of matched points.

(10) Interpolate the resulting sparse 3-D dataset if necessary.

subsurface reconstruction

Since the depth of penetration by light into most biological surfaces is a function of the wavelength of the incident light, multispectral imaging may be used to estimate the depth and/or density of various subsurface structures or processes (e.q. erythema). First, an explicit or implicitly assumed model of the surface with its subsurface structures and/or processes is considered. Based on this model, even if only implicitly assumed, and based on additional a priori information and/or assumptions, an algorithm which approximates the estimation of depth, i.e. subsurface extent, and/or density of a structure or process, may be derived using a functional representation of this mathematical model. A linear or nonlinear combination of images, each representing light of a limited bandwidth of wavelengths, reflected from the surface and its subsurface layers and components, may be employed to approximate an image whose grey-scale values linearly represent a particular depth, density, or other characteristic of a subsurface structure or process.

As an oversimplified, sample embodiment of such a method, consider, for example, a simplified model of the optical properties of skin wherein (1) light is attenuated exponentially as it penetrates through the skin and wherein (2) melanin is of uniform density. Then, subject to the assumptions of the model and other implicit assumptions, the depth of melanin for each pixel may be approximated by subtracting the log of an image, obtained (or computed) at a short wavelength, from the log of one, obtained (or computed) at a longer wavelength. This is equivalent to taking the log of one image divided by the other. This may be performed sequentially for a set of multispectral pairs of images. For example, given images of skin obtained simultaneously through infrared, red, green, and blue bandpass filters, the log of the blue image may be subtracted from the log of the infrared image to obtain an image estimating the thickness of melanin in a subsurface region of skin that extends between the superficial depth of penetration of blue light and the deep penetration of infrared light. The thickness (or possibly density) of pigment contained in sequentially thinner subsurface regions may be estimated (subject to the implicit assumptions) by (i) subtracting the log of the green image from the log of the infrared image to obtain a medium thickness subsurface estimate, and (ii) subtracting the log of the red image from the log of the infrared image.

Using the method of spectral projection described above under pre-processing 316, a potentially infinite number of images, each computed for a different wavelength in the visible spectrum, may be calculated. Via sequential log subtraction of these images from the log of the infrared image, a series of images representing the depth (and/or density) of pigment in subsurface slices of progressively increasing depth with decreasing thickness may be obtained. These may then be further manipulated to estimate pigment depth and/or density, or to estimate features of other subsurface structures or processes.

Alternative embodiments of the above method may be obtained by employing a more accurate mathematical model of the attenuation, scattering, and reflection of light of various wavelengths by a biological surface, such as the skin or retina.

Surface Segmentation (320)

Segmentation is the process by which an image of a surface is segmented into two or more regions, for example, regions representing artifact or interfering structures which must be detected and eliminated from subsequent analysis, regions of interest which will subsequently be analyzed, regions of background surface, and subregions within the regions of interest which will be eliminated from subsequent analysis. Segmentation may be applied to 2-D, 3-D, 4-D (space+time), R,G,B,H,S,I,Y,I, and/or Q images or any scalar or vector spectral derivative thereof.

When the invention is applied to the human cutaneous surface in vivo, the resulting images of skin may be segmented into regions of lesions and background skin. However, hairs may interfere with this part of the segmentation process, and may need to be detected and eliminated from this part of the segmentation process. In addition, specular reflections within regions representing lesions of interest may also require detection prior to subsequent quantitative feature extraction. The borders outlining these various image segments may also be computed during the surface segmentation process 320. Thus the segmentation process may include one or more of several steps which may be predetermined by he initialization routine or chosen by the operator 330 during the setup routine or during the analysis if so required or desired.

lesion detection

The basic segmentation between regions of interest (e.g. lesions) and regions of background surface may be performed in a number of ways. One method employs the following steps:

(1) Transform the vector R-G-B color image to one or more scalar images of a color space variable, as described in the pre-processing step 316 above, for example intensity, hue, saturation, luminance, chrominance, red, green, and/or blue.

(2) For one or more scalar transformed image compute local histogram estimates within finite 2-dimensional non overlapping windows.

(3) Smooth each local histogram estimate, for example with a robust nonlinear smoother such as "53H twice" (which sequentially convolves the histogram with a 5-point median window, followed by a 3-point median window, followed by a 3-point Hanning window and then repeats this sequence of convolutions a second time).

(4) Detect local extrema in the smoothed local histogram. The smoothing performed in the previous step makes this step less sensitive to noise in local histogram estimates computed within a small window.

(5) Classify each local histogram as either bimodal or non-bimodal based on location and magnitude of its local extrema.

(6) Compute a local threshold value between the two peaks of each bimodal histogram. If no bimodal histograms were detected change the size of the data window and then repeat steps 2-6 above).

(7) Compute a global threshold value based on the local threshold values computed only for those regions of the image that have bimodal histograms, or alternatively interpolate local theshold values for image regions that have non bimodal histograms.

(8) Segment the image into two regions with this global threshold, or alternatively segment the image with the local thesholds determined above, resulting a binary image consisting of regions of the image whose pixel values are above the threshold and regions whose pixel values are below the threshold.

blob detection (9) Perform morphological "blob" detection to further segment the binary image into distinct regions of contiguous pixels ("blobs") which are either below or above the threshold. Blobs with pixel values below the threshold represent regions of interest (i.e. lesions or foreground) whereas blobs with pixel values above the threshold represent regions of background surface and/or specular reflections within lesions (i.e. nonlesions). This definition of foreground and background regions may be reversed as determined by the initialization and setup routines or by image features extracted by the analysis routines.

(10) Count the number of blobs representing lesions (foreground) and the number of blobs representing nonlesions (background).

(11) Determine the size (i.e. area) of each lesion and nonlesion blob.

(12) Eliminate all except the n largest foreground blobs representing lesions (satellite elimination), where n is a predetermined number set during initialization, setup, or during a previous analysis step; or alternatively use a predetermined size, rather than number, n, as the elimination criterion.

(13) Eliminate (and record the location and extent of) all except the n largest nonlesion blobs.

(14) Record the location and extent of all nonlesion blobs which are contained within lesion blobs. These may be used as candidate regions for specular reflections.

(15) Compute the edges of the foreground blobs which represent lesions, for example by seaching for horizontal and vertical binary gradients (i.e. binary transitions).

Thus the image of the surface is segmented into regions representing regions of interest (lesions), regions of specular reflections within these regions of interest, and regions representing "normal" background.

The results of this segmentation method, when performed on more than one color space variable, may be combined for certain applications.

Alternatively, steps 1-8 of the above "lesion detection" segmentation may be performed by computing global histograms of the number of pixels of each intensity (or other color space variable) and then automatically or manually (using the mouse 111 or keyboard 112) setting the threshold at the nadir between the two modes of the histogram distribution if it is bimodal.

segmentation with prior elimination of structures with known a priori features

Surface structures with known a priori features may be detected and eliminated prior to the "lesion detection" segmentation step decribed above. For example, for the human cutaneous surface, hairs may interfere with segmentation. Therefore, a prior segmentation step designed to detect and eliminate hair, may be performed before lesion detection. As a sample embodiment of such a method, consider the following steps:

segmentation with prior hair elimination (1) Given one or more color space transformations of the original image (Transformed Image), as described in the pre-processing step 316, (2) perform an appropriate grey-scale morphological closing operation (a set of ordered statistic operations) on the Transformed Image to obtain an estimate of an image without hair denoted the Less Hair Image. This closing may be implemented as the concatenation of a set of grey scale closings, for example, four concatenated grey scale closings, each with a different structuring element. The structuring elements used in the closing operations should incorporate some a priori information about known features of human hair in images obtained at a given surface magnification. For example, four linear structuring elements, each at a different orientation angle may be sequentially applied. The maximum diameter of the resulting equivalent concatenated structuring element should, for example, be greater than or equal to the width of the majority of hairs in the image. Note that under most circumstances this method results in better hair elimination for image regions where hair is superimposed over background normal skin, than for image regions where hair overlies a lesion.

The Less Hair Image may alternatively be obtained using a threshold type of segmentation (e.g. "lesion detection" segmentation steps 1-8) applied to a hue transformation of the original R-G-B image or to an intensity transformation of the original R-G-B image followed by a color space projection onto the mean hue color vector for a known image region containing only hair (see Pre-processing 316).

(3) Subtract the Less Hair Image from the original Transformed Image to obtain an image denoted as the Hair Only Image.

(4) Perform a "lesion and blob detection" segmentation (steps 1-14 above) on the Hair Only Image to obtain a Binary Hair Only Image.

(5) Perform a "lesion and blob detection" segmentation (steps 1-14 above) on the Less Hair Image to obtain a Binary Less Hair Image.

(6) Pixels which are in the Binary Hair Image and not in the Binary Less Hair Image are considered to be hair external to the border of the lesion.

(7) Pixels which are both in the Binary Hair Image and in the Binary Less Hair Image are considered to be hair that is within the borders of the lesion and which are then eliminated from subsequent quantitative feature extraction analysis 322.

(8) Construct a Hybrid Image consisting of two regions separated by a border determined by edges of the Binary Less Hair Image. These edges are obtained by applying blob detection step 15 above to the Binary Less Hair Image. The region outside this edge border is replaced by the original Less Hair Image, and the region within the edge border is replaced by the original Transformed Image. This resulting Hybrid Image thus contains an image without hair outside the border and the original raw image with hair inside the border.

(9) The border will under most circumstances be a closed contour which contains the true lesion border within it, due to properties of the "lesion detection" segmentation method above when applied to an image containing hair. Thus the final step consists of applying the "lesion and blob detection" segmentation method (steps 1-15 above) to the Hybrid Image to obtain a more accurate estimate of the true border of the lesion.

(10) The pixel locations determined in step 7 immediately above denote the location of hair covering the lesion, and are used to eliminate these pixels from subsequent feature extraction 322.

Quantitative Feature Extraction (322)

Once the borders of lesions are obtained by segmentation 224, quantitative features of the images may be computed 226.

Features of the Global Surface number of lesions

The number of lesions in a image, or reconstructed map, of a surface may be counted using morphological image processing methods with steps similar to those described in the "blob detection" segmentation (steps 9-14) described above 320.

location of lesions

The location of lesions on the surface may be graphically represented on a set of low magnification (global) views of the surface. These locations are determined by the 3-D location parameters input by the position sensor 152 when a higher magnification (local) view of a lesion on the surface was acquired. A straightforward geometric transformation may be applied to correct for the distance between the mounting position of the position sensing element 324 and the center of the local region of anatomic surface which was imaged. These coordinates are then mapped onto the global or reference image of the surface using data obtained during calibration of the position sensor coordinates to the pixel location coordinates on the global or reference image.

Alternatively, rather than use a global or reference digital photographic image, a standardized synthetic body surface map (with graphical display) may be employed. Moreover, if this surface map can be parameterized, then the locations of individual lesions, may be represented as quantitative values representing the location on the surface map.

3-D and 4-D surface morphology and topology

Morphological and topological features of a 3-D surface map (or 4-D time varying 3-D surface map), obtained during the surface reconstruction step 318 above, may be quantified. For example, surface elevation statistics (e.g. mean, mode, variance, skewness) may be obtained via straightforward computation. Topological features, such as the number of peaks in surface elevation that are above a certain threshold, may be counted; or given any binary threshold of surface elevation, the Euler number of the resulting binary surface, defined by this threshold, may be computed using binary image processing methods (similar to the "blob detection" step described above), and may be used as a parameter describing surface texture.

Features of Local Surface Lesions

Once lesions on the anatomic surface are detected by the segmentation algorithms 320, their morphologic and spectral features are determined and represented as a set of quantiative parameters. For surfaces such as the skin, quantitative descriptors of lesion asymmetry, border irregularity, color, diameter, elevation, and texture may be of clinical importance.

Asymmetry

Quantitative features of a 2-dimensional lesion which describe its asymmetry are roundedness (defined as the ratio of the minimum to maximum second moment of the lesion about its centroid), and eccentricity (defined as the ratio of the major to minor axis of the lesion). Roundedness is multiplied by 100 to present it as a percent varying between 100% for a perfect circle and 0% for a straight line.

Border irregularity

Border irregularity may be determined by the following parameters:

(1) Radial or polar statistics—Given a polar representation of the border (i.e. one that parameterizes the distance between the centroid of the lesion to the border as a function of the angle above the horizontal), statistics may be defined, for the distribution of this radial distance, over all angles from 0 to 360 degrees. For example, the standard deviation of this radius may be used to quantify radial border irregularity.

(2) Convex deficiency of the border—First the convex hull of the lesion is computed using the following algorithm:
  (i) Determine the point where the longest ray from the lesion centroid intersects the lesion border.
  (ii) Beginning with this point, compute straight lines which extend at an angle that is progressively incremented until a line is obtained which intersects another pixel on the identified lesion border.
  (iii) Connect the points of intersection with the border.
  (iv) Repeat steps (ii) and (iii) until a closed contour is obtained or until the point identified in step (i) is reached.

If the angle increment in step (ii) is small enough an excellent approximation of the convex hull of the lesion's border will be obtained. The convex deficiency of the border is then obtained by subtracting the area of the lesion (i.e. the number of pixels or square millimeters obtained within the border) from the area within the convex hull. This is then normalized by dividing it by the area of the lesion and then multiplying it by 100. The convex deficiency of the border thus quantifies the area of any concave indentations into the lesion as a percentage of the lesion's area.

(3) Inverse compactness—A parameter related to the compactness of a lesion's border is defined using the square of the perimeter of the border divided by the area within the border. This dimensionless number is approximately 12 for a perfect circle and rapidly increases for borders with finger-like extensions.

(4) Fractal dimension—The fractal dimension, fd, of the border is estimated by first superimposing a rectangular grid over the image. The size of boxes defined by the grid may be as small as a single pixel or may be larger. Let N be defined as the number of grid boxes which contain pixels on the lesion's border. Let r be defined as the width of a single grid box divided by the maximum diameter of the lesion. Then the fractal dimension of the border is estimated by dividing the log of N by the log of 1/r. Estimates of the fractal dimension may be obtained for more than one grid size and then averaged.

(5) Distinctness of the border—Parameters, which are related to how distinct the border is relative to the region just inside and outside the determined border, may be estimated using a variety of statistics, including statistics derived from gradients of image intensity, hue, or saturation at the border, border entropy, and/or border energy.

Color

The color of each pixel within the border of a lesion may be quantified by its hue (as a number from 0 to 360 degrees, or, if properly calibrated, as a wavelength in nanometers) and by its saturation (as a percent between 0 and 100%). The distribution of colors within the identified boundaries of a lesion may be represented as a set of points on a color wheel which displays all possible colors (of the given color space model) at a given level of intensity, such as the mean intensity for the pixels within the lesion boundary. The distribution of pixel colors within the lesion border may also be displayed as individual histograms of hue and saturation, or as a 2-dimensional joint histogram of hue and saturation. Quantitative parameters may be extracted from these graphical presentations of color distribution, including the mean, mode, standard deviation, and other statistics of the hue and/or saturation. Regions within the lesion that were identified as specular reflections or interfering structures, such as hair, are excluded from this color analysis.

Diameter and Area

The diameter of a lesion may be computed as the maximum and minimum diameter through the centroid of the lesion. The area is computed by counting the number of pixels within the border and then multiplying by the scale factor determined in the spatial calibration sequence above.

Elevation

If 3-dimensional surface reconstruction was performed above 318, then quantitative parameters that describe features of the elevation of the surface may be computed such as statistical features of surface elevation (i.e. mean elevation, standard deviation, variance, kurtosis, and other moments of the elevation, as well as histogram and spectral density of the elevation).

Other morphologic features

Profiles

Profiles of any scalar value, such as intensity, hue, or saturation, may be displayed as a function of x and y image position, resulting in a pseudo-3-D plot.

Texture

A variety of standard or novel quantative parameters may be used to characterize the texture of any scalar or vector image region. This may be particularly important in characterizing spatial distributions of pigment in skin lesions.

Multispectral features

A multispectral color wheel using the multispectral generalization of the HSI color space transformation, described in pre-processing 316, may be used to plot generalized multispectral distributions of hue and saturation and to calculate statistics thereof. Multispectrally derived features, such as relative lesion depth and volume, may be computed using information derived from the subsurface reconstruction method described above in system function 318. Estimation of such features may be improved further by incorporating information about surface elevation derived from the surface reconstruction methods also described above in system function 318.

A variety of other spectral algorithms, related to algorithms used for example to detect relative amounts of various substances with known spectral properties (e.g. hemoglobin, melanin, bilirubin in skin) may be applied to multispectral images of visually accessible anatomic surfaces.

Classification (324)

Given a set of quantitative features of lesions or other structures or processes on an anatomic surface, these features may be used to classify tee lesions, structures, or processes into one or more classes. Standard methods of classification, decision making, or clustering may be used, depending on the type and amount of a priori information available about each of the potential classes and about each of the lesions, structures, or processes on the anatomic surface.

For example, given some a priori information about how morphologic and spectral features of pigmented cutaneous lesions correlate with microscopic pathologic features thereof, a classification method may be employed by the invention that incorporates this a priori information into a classification scheme that would estimate the probability that a given cutaneous lesion belonged to a particular pathologic class or diagnosis.

Or, for example, consider multispectral data, and a priori information about the known spectral properties of certain pigments and other structures in the skin, then, a classification scheme could be employed by the invention that would classify each pixel as belonging to one, or possibly more than one, class representing, for example, melanin, oxyhemaglobin, deoxyhemaglobin, bilirubin, or nonpigmented skin.

Numerous variations on these methods and classification schemes may be implemented by the invention.

Database (326)

Once lesions on, or regions of, the anatomic surface are detected by the segmentation algorithm 320, their morphologic, spectral, or other features are determined and represented as a set of quantitative parameters 322. These quantitative parameters are stored in a database 326 along with the original and processed images, all acquisition and processing parameters, and clinical data provided by the patient and physician. Information in the database 326 may be used for subsequent temporal comparison, tissue classification, or clinical decision making.

The database 326 automatically records all protocols and parameters used during image acquisition 312, processing 314,316,318,320,322,324, storage 326, display 328, and if used, control 332. It thus stores all internal parameters describing where each image is stored. It also stores a miniature version of each image, called an image icon. The database 326 does all of the internal record keeping necessary for efficient storage, analysis, and display. Data, including all images, may be recovered from the database by the operator 330 using a graphical screen interface with a mouse 111 or other input device, e.q. 131, with a structured query language, or via other software means.

A sample embodiment of a database structure 326 includes three main types of data records—patient records, acquisition records, and image records. A patient record contains all clinical information about the patient and points to all acquisition records associated with the patient. An acquisition record contains all acquisition information and points to all images taken during a particular acquisition session. An image record contains (1) filenames and locations of all images associated with the record, (2) all extracted features of the images in the record along with the particular choice of methods and parameters used to obtain them, and (3) location with respect to global or reference image of each image in the record.

Display and hardcopy (328)

Various types of 2- or 3-dimensional video or graphic displays may be employed to display high resolution, true color, and/or multispectral images and extracted features thereof. A liquid crystal stereoscopic display may be used to display 3-D data or stereo images, or, for example, a reconstructed 3-D surface may be rendered and displayed as a shaded object viewed from an arbitrary perspective. Holographic or computer-generated holographic displays may also be employed when available.

Simultaneous visual presentation of a set of global, reference images may be displayed with a superimposed graphical map of the location on the surface of local images. This map may be color coded to a set of image icons of local images which are simultaneously displayed on the same screen. The operator 330 may select an image icon, using a pointing device 111, to automatically view the full size version of this image, to control processing and analysis, and to display any or all extracted features thereof.

A hardcopy unit 146, such as a continuous tone, high resolution, digital color printer, may be used to obtain a hardcopy of any screen displayed on the monitor 144 including images and data.

Decision & control (332)

Having thus obtained images of anatomic surfaces and quantitative features and classifications thereof, this information may be used either directly by the invention, or indirectly by the physician scientist, or operator 330 to either (1) assist in clinical decision making and patient management, (2) assist in other decision making, such as the choice of a cosmetic of the appropriate color, or (3) to provide a control signal input to an instrument or apparatus such as a computer-controlled laser angioplasty device. Assistance to a physician may be rendered not only by supplying quantitative information about lesions on the surface but also by providing information in the form of stored images and clinical data of the appearance of the lesion in the past.

Having shown the preferred embodiment, those skilled in the art will realize many variations are possible which will still be within the scope and spirit of the claimed invention. Therefore, it is the intention to limit the invention only as indicated by the scope of the claims.

What is claimed:

1. An apparatus for monitoring visually accessible surfaces of the body comprising:
    means for acquiring digital images;
    means for pre-processing said digital image to calibrate and correct for aberrations in the digital image;
    means for determining or estimating a three-dimensional representation of the surface of which the image is taken;
    means for estimating the boundaries of lesions on said surface from said image;

means for extracting two- and three-dimensional quantitative features of the lesions on said surface from said image;

means for visual display and hardcopy presentation of two- dimensional and reconstructed three-dimensional representations of the lesions on said surface;

means for storing said digital images in a database; and means for extracting information from the database for comparison of images at different points in time or space.

2. The apparatus according to claim 1 further a plurality of lighting means.

3. The apparatus according to claim 2 wherein lighting means are spatially uniform.

4. The apparatus according to claim 2 wherein the lighting means are structured.

5. The apparatus according to claim 2 wherein the lighting means are monochromatic.

6. The apparaturs according to claim 2 wherein the lighting means are natural ambient light.

7. The apparatus according to claim 1 wherein the image acquisition means is a CCD (charge coupled device).

8. The apparatus according to claim 1 wherein the image acquisition means is a high resolution video camera.

9. The apparatus according to claim 1 wherein the image acquisition means is a laser scan camera.

10. The apparatus according to claim 1 wherein the image is multispectral.

11. The apparatus according to claim 1 wherein the image is obtained through a filter.

12. The apparatus according to claim 1 wherein the acquired images are obtained from a single view.

13. The apparatus according to claim 1 wherein the digital images are obtained from a plurality of views.

14. The apparatus according to claim 1 wherein the digital images are obtained from more than one simultaneous view.

15. The apparatus according to claim 1 wherein the digital images are obtained from a plurality of sequential views.

* * * * *